(12) United States Patent
Vyshedskiy

(10) Patent No.: US 9,610,042 B1
(45) Date of Patent: Apr. 4, 2017

(54) DETECTING A MEDICAL CONDITION USING A MOBILE COMPUTING DEVICE

(71) Applicant: Andrey Vyshedskiy, Brookline, MA (US)

(72) Inventor: Andrey Vyshedskiy, Brookline, MA (US)

(73) Assignee: Iosif M. Gershteyn, Newton, MA (US)

( * ) Notice: Subject to any disclaimer, the term of this patent is extended or adjusted under 35 U.S.C. 154(b) by 230 days.

(21) Appl. No.: 14/532,779

(22) Filed: Nov. 4, 2014

Related U.S. Application Data

(60) Provisional application No. 62/071,013, filed on Sep. 12, 2014.

(51) Int. Cl.
| | |
|---|---|
| A61B 5/02 | (2006.01) |
| A61B 5/00 | (2006.01) |
| A61B 7/00 | (2006.01) |
| A61B 7/04 | (2006.01) |
| A61B 5/113 | (2006.01) |
| A61B 5/11 | (2006.01) |
| A61B 5/01 | (2006.01) |
| A61B 5/087 | (2006.01) |

(52) U.S. Cl.
CPC .............. *A61B 5/6898* (2013.01); *A61B 5/01* (2013.01); *A61B 5/087* (2013.01); *A61B 5/1101* (2013.01); *A61B 5/1135* (2013.01); *A61B 5/7282* (2013.01); *A61B 5/746* (2013.01); *A61B 7/003* (2013.01); *A61B 7/006* (2013.01); *A61B 7/008* (2013.01); *A61B 7/04* (2013.01)

(58) Field of Classification Search
None
See application file for complete search history.

(56) References Cited

U.S. PATENT DOCUMENTS

| | | | |
|---|---|---|---|
| 5,218,969 A | 6/1993 | Bredesen et al. | |
| 5,717,769 A | 2/1998 | Williams | |
| 5,844,995 A | 12/1998 | Williams | |
| 7,043,292 B2 * | 5/2006 | Tarjan ................. | A61B 5/0408 600/509 |
| 8,200,277 B2 | 6/2012 | Lee | |

(Continued)

OTHER PUBLICATIONS

V.I. Korenbaum, "Features of Acoustic Processes in Human Respiratory System," Institute of Physics and Information Technologies, Far Eastern State University, 8, Sukhanov St., Vladivostok, 690600, Russia, 1999, retrieved from: www.akin.ru/Docs/Rao/Ses10/Me1.PDF (Nov. 11, 2014).

(Continued)

*Primary Examiner* — Sunit Pandya

(57) ABSTRACT

Systems and methods for detecting a medical condition using a mobile computing device are provided. In some aspects, a computer receives sound measurements generated at a microphone. The computer receives thorax movement measurements recorded by a motion measurement unit in parallel with recording the sound measurements at the microphone. The computer determines a relationship between the sound measurements and the thorax movement measurements. The computer determines a medical condition based on the relationship between the sound measurements and the thorax movement measurements. The computer provides an output representing the medical condition.

15 Claims, 5 Drawing Sheets

(56) References Cited

U.S. PATENT DOCUMENTS

| | | | | |
|---|---|---|---|---|
| 8,923,918 | B2* | 12/2014 | Kreger | A61B 5/02433 455/554.2 |
| 9,042,168 | B1 | 5/2015 | Yang | |
| D746,802 | S | 1/2016 | Mulumudi | |
| 9,414,155 | B2 | 8/2016 | Mulumudi | |
| 2006/0195342 | A1* | 8/2006 | Khan | G06Q 10/10 705/3 |
| 2008/0306367 | A1* | 12/2008 | Koehler | A61B 5/4255 600/364 |
| 2012/0283581 | A1* | 11/2012 | Olde | A61B 5/02 600/485 |
| 2013/0170686 | A1 | 7/2013 | Lester | |
| 2016/0192846 | A1* | 7/2016 | Shekhar | A61B 5/02028 600/528 |
| 2016/0210747 | A1* | 7/2016 | Hay | A61B 5/4815 |

OTHER PUBLICATIONS

Matthew Kinney, "Medical Acoustics Announces the Appointment of Sensormedics Italia as Master Distributer for Europe, Middle East and North Africa," NASDAQ Globe Newswire, Feb. 6, 2014, retrieved from: globenewswire.com/news-release/2014/02/06/608213/10067369/en/Medical-Acoustics-Announces-the-Appointment-of-Sensormedics-Italia-as-Master-Distributor-for-Europe-Middle-East-and-North-Africa.html (Nov. 11, 2014).

Ram Mor, MD, et al., "Breath Sound Distribution Images of Patients with Pneumonia and Pleural Effusion," Respiratory Care, Dec. 2007, vol. 52, No. 12, pp. 1753-1760.

Raymond LH Murphy, MD, et al., "Automated Lung Sound Analysis in Patients with Pneumonia," Respiratory Care, Dec. 2014, vol. 49, No. 12, pp. 1490-1497.

Andrey Vyshedskiy, PHD, et al., "Mechanism of Inspiratory and Expiratory Crackles," Chest Journal, 2009, 135:156-164.

Office Action of U.S. Appl. No. 14/532,820 dated Aug. 23, 2016.

* cited by examiner

DETECTING A MEDICAL CONDITION USING A MOBILE COMPUTING DEVICE

CROSS REFERENCE TO RELATED APPLICATIONS

This application claims priority under 35 U.S. C. §119(e) and the benefit of U.S. Provisional Application No. 62/071,013, filed Sep. 12, 2014, and entitled, "A sleeve attachment for converting a smartphone into a stethoscope," the entire disclosure of which is incorporated herein by reference. This application is related to U.S. patent application Ser. No. 14/532,820, being filed concurrently herewith, and entitled, "SYSTEM AND METHOD FOR DETECTING A MEDICAL CONDITION USING A MOBILE COMPUTING DEVICE," the entire disclosure of which is incorporated herein by reference.

BACKGROUND

The subject technology is generally directed to systems and methods for generating a medical diagnosis using a mobile computing device.

Over 1.2 million children died from pneumonia in 2011. Amoxicillin is an effective antibiotic with activity against the pneumococcus. However, children with pneumonia in developing countries face many obstacles that impede their access to timely and appropriate treatment. Such obstacles include inability of caregivers to recognize signs and symptoms of the disease. As the foregoing illustrates, approaches to improve and simplify pneumonia diagnosis are desirable.

Furthermore, patients with other diseases, such as asthma, congestive heart failure, chronic obstructive pulmonary disease (COPD), bronchitis, tuberculosis, acute respiratory distress syndrome, cystic fibrosis, bronchiolitis, asbestosis, intestinal obstruction or cardiac abnormalities, may also experience symptoms and require help when medical professionals are not available. As the foregoing illustrates, a new approach for detecting medical conditions at the point-of-care and providing a treatment recommendation to a patient suffering from disease symptoms may be desirable.

SUMMARY

In some aspects, a system is provided. The system includes a housing for holding a mobile computing device against a human skin. The housing includes a skin connector piece for placing against the human skin. The skin connector piece includes a bell having an apex and a cavity. The housing includes a sleeve connected to the skin connector piece adjacent to the apex of the bell. The sleeve includes a first aperture for accepting the mobile computing device and for placing a microphone of the mobile computing device at the apex of the bell.

In some aspects, a system is provided. The system includes one or more processors and a memory. The memory includes instructions which are executed by the one or more processors. When executing the instructions, the one or more processors receive sound measurements recorded at a microphone. The one or more processors receive thorax movement measurements recorded at a motion measurement unit concurrently with recording the sound measurements at the microphone. The one or more processors determine a relationship between the sound measurements and the thorax movement measurements. The one or more processors determine a medical condition based on the relationship between the sound measurements and the thorax movement measurements. The one or more processors provide an output representing the medical condition.

In some aspects, a non-transitory computer-readable medium is provided. The non-transitory computer-readable medium stores instructions. The instructions include code to receive sound measurements recorded at a microphone. The instructions include code to receive thorax movement measurements recorded at a motion measurement unit in parallel with recording the sound measurements at the microphone. The instructions include code to determine a relationship between the sound measurements and the thorax movement measurements. The instructions include code to determine a medical condition based on the relationship between the sound measurements and the thorax movement measurements. The instructions include code to provide an output representing the medical condition.

In some aspects, a computer-implemented method is provided. The method includes receiving, at one or more processors, sound measurements recorded at a microphone. The method includes receiving thorax movement measurements recorded at a motion measurement unit in parallel with recording the sound measurements at the microphone. The method includes determining a relationship between the sound measurements and the thorax movement measurements. The method includes determining a medical condition based on the relationship between the sound measurements and the thorax movement measurements. The method includes providing, at a display unit, an output representing the medical condition.

BRIEF DESCRIPTION OF THE DRAWINGS

Features of the subject technology are set forth in the appended claims. However, for purpose of explanation, several aspects of the disclosed subject matter are set forth in the following figures.

DETAILED DESCRIPTION

Figure 1:
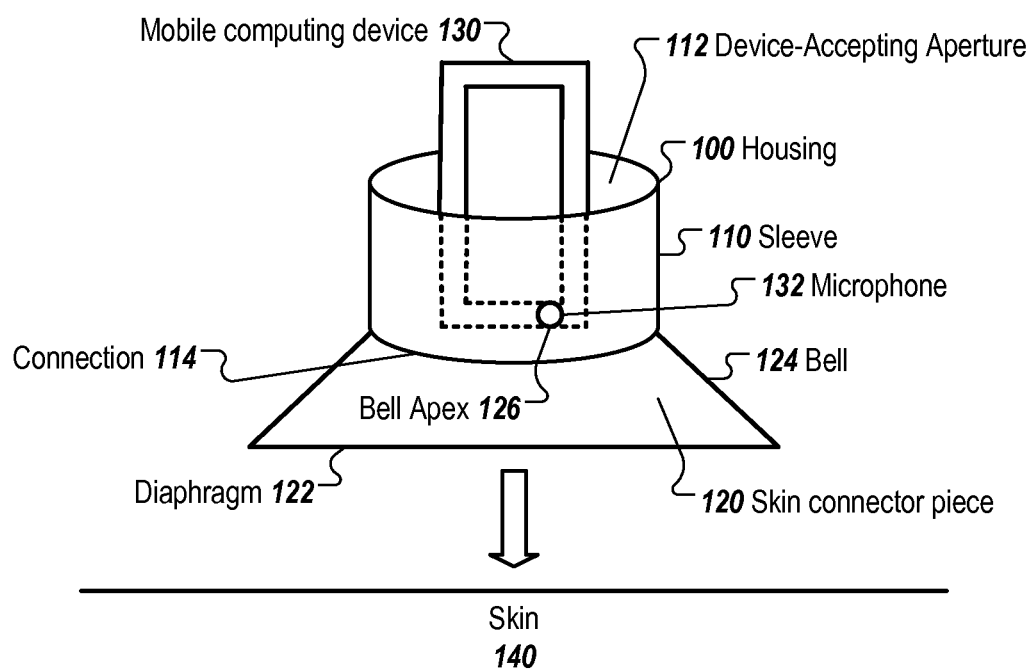
FIG. 1 illustrates an example of a housing for holding a mobile computing device against a human skin.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent that the subject technology is not limited to the specific details set forth herein and may be practiced without these specific details. In some instances, certain structures and components are shown in block diagram form in order to avoid obscuring the concepts of the subject technology.

As set forth above, a new approach for providing a treatment recommendation to a patient suffering from disease symptoms may be desirable. The subject technology, in some implementations, provides techniques for providing a treatment recommendation to a patient suffering from disease symptoms. The treatment recommendation may include, for example, a diagnosis of a disease, a recommendation to take or administer a medication, or a recommendation to visit a physician immediately or in the near future.

A stethoscope is widely used by medical personnel to listen to body sounds using a process called auscultation. Auscultation may be significantly facilitated by a mobile computing device including a processor, a memory, and a microphone, for example, a smartphone. The mobile computing device, when used as a stethoscope, may detect, visualize and sort abnormal sounds such as crackles, wheezes, and heart murmurs. A mobile computing device can also assist medical personnel in diagnosing and treating a patient. Furthermore, consumers who are not medical professionals may use a mobile computing device to collect and telemeter their own lung and heart sounds or the lung and heart sounds of someone they are taking care of, such as an elderly relative.

In some implementations, the subject technology may be used for early diagnosis of pneumonia, possibly leading to reducing mortality through timely use of antibiotics. One early indication of pneumonia is provided by lung sounds. Crackles and squawks appear in the lungs up to several days before changes become visible on X-Ray or Computerized Tomography (CAT scan). In another implementation, the subject technology may be used for asthma monitoring, to detect early signs of asthma attack and thereby prevent a full blown asthma attack. In yet another implementation, the subject technology may be used for crackle monitoring in Congestive Heart Failure (CHF) patients. As CHF gets worse, the number of crackles may increase and the quality of the crackles may change.

In some cases, implementations of the subject technology may be used to reduce bad (unnecessary) hospital visits through telemetry, and increase useful visits to medical professionals or treatment facilities, which are essential for timely medical intervention. As a result, emergency hospital visits may be reduced.

Some implementations of the subject technology are directed to an inexpensive smartphone sleeve attachment that allows the smartphone to function as a device that diagnoses medical condition(s) based on sound measurements and thorax movement measurements. The sound measurements and the thorax movement measurements may be taken from a person's skin or a position immediately outside the person's skin. After taking some measurements and with appropriate permissions from the user, the device may transmit information over the web, and a diagnosis may be made at a server or in consultation with a physician.

In some implementations, a sleeve, which may be made of plastic or rubber, may be connected to a mobile computing device, thus converting the mobile computing device into a chest piece. A microphone of the mobile computing device is used to records lung sounds, while a motion measurement unit of the mobile computing device is used to identify inspiration and expiration. For example, to detect pneumonia, a caregiver may apply the mobile computing device to several (e.g., between 8 and 12) locations over the thorax while guided by verbal instructions generated by the mobile computing device or instructions displayed through a display unit of the mobile computing device. The instructions may be displayed on all of the display unit or on a part of the display unit (e.g., half of the display unit) that is not covered by the sleeve or a hand of the user. The verbal instructions may be played through a speaker or a headphone jack of the mobile computing device. Crackles or squawks consistently detected over several breaths may be used, by the mobile computing device, to identify the presence of pneumonia. Alternatively, the logic to identify the presence of pneumonia may reside at the server. As used herein, the phrase "motion measurement unit" encompasses its plain and ordinary meaning including, but not limited to, any device or component that measures position, speed, velocity, acceleration, rate of change of acceleration, etc. A motion measurement unit may include one or more of a speedometer, an accelerometer, a gyrometer, an inclinometer, etc.

To operate some implementations of the subject technology, a user may slide the sleeve attachment over one end of a mobile computing device, then press the mobile computing device against the patient's skin, and then follow the instructions provided by the mobile computing device.

As used herein the term "patient" encompasses its plain and ordinary meaning including, but not limited to, a person who is believed to have a disease or to be "sick," and who is being cared for by medical personnel, such as doctor(s) or nurse(s), by caregivers who are not trained in medicine, such as family member(s), or by himself.

FIG. 1 illustrates an example of a housing 100 for holding a mobile computing device 130 against a human skin 140. The mobile computing device 130 may be any mobile computing device, for example, a mobile phone, a smartphone, a tablet computer, a personal digital assistant (PDA), a personal digital music player, a laptop computer, etc. As shown, the housing 100 includes a sleeve 110 and a skin connector piece 120.

The sleeve 110 includes a device-accepting aperture 112 and a connection 114. The connection 114 connects the sleeve 110 to the skin connector piece 120. The device-accepting aperture 112 allows the mobile computing device 130 to be placed inside the sleeve 110. The sleeve 110 may roll onto the mobile computing device 130. Alternatively, the sleeve 110 may include the device-accepting aperture 112 for receiving/holding the mobile computing device 130, such that the user may place the mobile computing device 130 into the device-accepting aperture 112.

The skin connector piece 120 includes a diaphragm 122 and a bell chamber 124. The diaphragm 122 may be placed adjacent to the human skin 140 to operate the mobile computing device 130 to take sound and thorax movement measurements. The bell 124 has an apex 126. When the mobile computing device 130 is inside the sleeve 110, the bell apex 126 is positioned proximate or adjacent to a microphone 132 of the mobile computing device 130. The diaphragm 122 and the bell 124 are used to channel acoustic vibrations of the human skin 140 to the microphone 132.

The skin connector piece 120 is for placing against the human skin 140. The skin connector piece includes the bell 124 having the apex 126 and a covering membrane at a cavity of the bell 124. The covering is opposite the apex 126 of the bell 124. The covering may be the diaphragm 122. The sleeve 110 is connected to the skin connector piece 120 using the connection 114 and adjacent to the bell apex 126. The sleeve 110 includes a device-accepting aperture 112 for accepting the mobile computing device 130 and for placing a microphone 132 of the mobile computing device 130 at the bell apex 126.

According to some implementations, the bell 124 may be made of hard plastic, and the sleeve 110 may be made of soft plastic, rubber or polyurethane. Alternatively, the bell 124 and the sleeve 110 may be made of the same material. An outside portion of at least one of the skin connector piece 120 or the sleeve 110 may include a noise insulating material to prevent or reduce the entry of outside noise into the microphone 132. The noise insulating material may be foam, rubber, a bubbly material, or any other noise insulating material.

According to some implementations, the sleeve 110 and the skin connector piece 120 are airtight for channeling acoustic vibrations from the human skin 140 to the microphone 132 of the mobile computing device 130. The sleeve 110 may include a stopper to prevent sliding of the mobile computing device 130. In some cases, a distance between the bell apex 126 and a covering membrane at the cavity of the bell 124 may be at least 2.5 centimeters (1 inch). The covering membrane at the cavity of the bell 124 may be the diaphragm 122. The diaphragm 122 may be a flat, thin or rigid membrane made of a an epoxy-fiberglass compound, or other suitable plastic.

Figure 2:
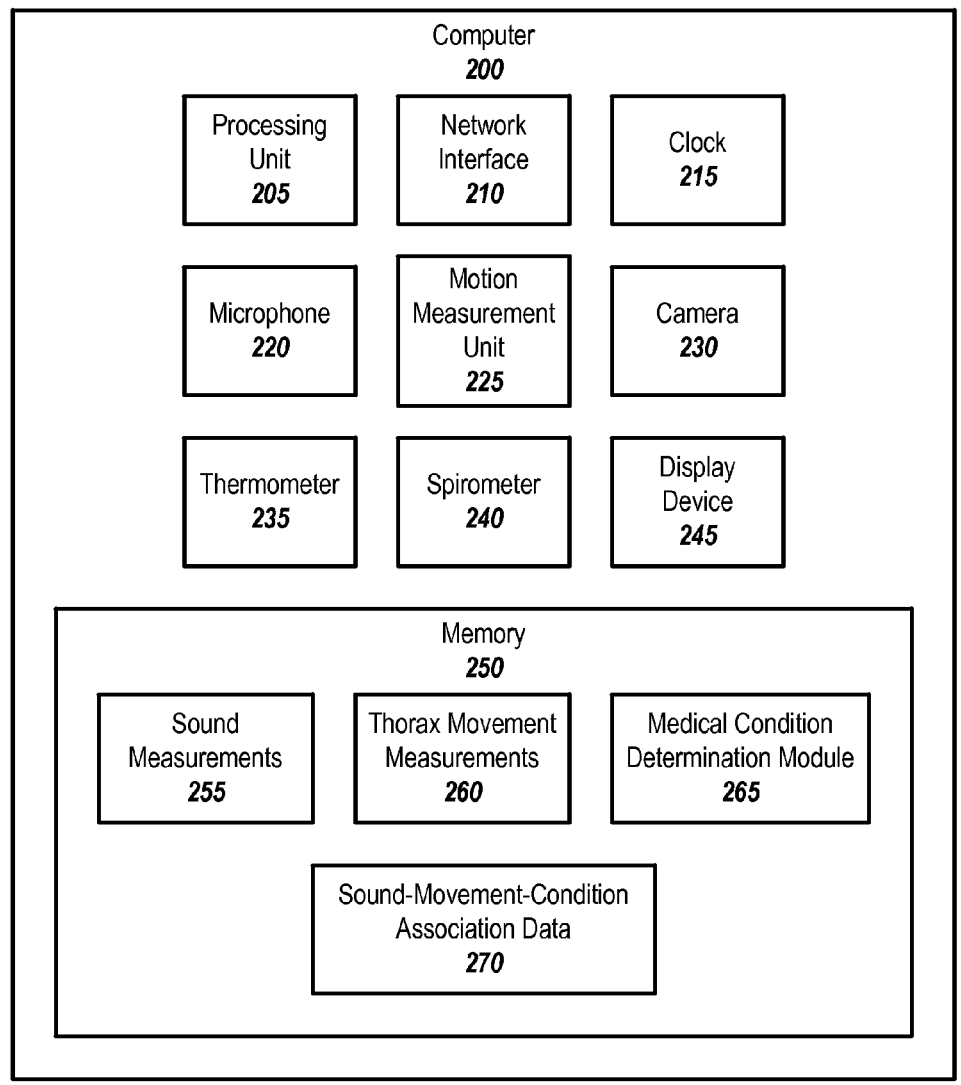
FIG. 2 illustrates, as a block diagram, an example of a computer for determining a medical condition based on sound measurements and thorax movement measurements.

FIG. 2 illustrates, as a block diagram, an example of a computer 200 for determining a medical condition based on sound measurements and thorax movement measurements. In some examples, the computer 200 corresponds to the mobile computing device 130 of FIG. 1, which is placed inside the housing 100. The computer 200 may be any mobile computing device, for example, a mobile phone, a smartphone, a tablet computer, a personal digital assistant (PDA), a personal digital music player, a laptop computer, etc.

Alternatively, a single "high-end" device may include the computer 200 coupled with the skin connector piece 120 of FIG. 1. The "high-end" device may be more expensive to manufacture than the housing 100. However, the "high-end" device may provide more precise or more exact measurements, which may be used for more precise or more exact diagnosis or treatment recommendations. The "high-end" device may be marketed to medical professionals, while the housing 100, which may be used together with a consumer mobile computing device, such as a smartphone, may be marketed to consumers who may not be medical professionals.

As shown in FIG. 2, the computer 200 includes a processing unit 205, a network interface 210, a clock 215, a microphone 220, a motion measurement unit 225, a camera 230, a thermometer 235, a spirometer 240, a display device 245, and a memory 250.

The processing unit 205 includes one or more processors. The processing unit may include a central processing unit (CPU), a graphics processing unit (GPU), or any other processing unit. The processing unit 205 is capable of executing computer instructions that are stored in a computer-readable medium, for example, the memory 250.

The network interface 210 allows the computer 200 to transmit and receive data in a network, e.g., the Internet, a cellular network, a local area network (LAN), a wide area network (WAN), a WiFi network, etc. The network interface 210 may include one or more network interface controllers (NICs).

The clock 215 stores a current time, which is updated once every threshold time period (e.g., once every second, once every 0.1 seconds, or once every 0.01 seconds). The clock 215 may be used to determine a current time or to determine a time difference between two moments.

The microphone 220 may correspond to the microphone 132 of FIG. 1. The microphone 220 may record sound(s), which may be stored in the memory 250 for further processing, analysis, or playback.

The motion measurement unit 225 measures position or movement. The motion measurement unit 225 may be used to measure position, velocity, acceleration, rate of change of acceleration, etc. The motion measurement unit 225 may include one or more of a speedometer, an accelerometer, a gyrometer, an inclinometer, etc. When the skin connector piece 120 or the computer 200 is placed adjacent to a patient's skin (e.g., human skin 140), the motion measurement unit may be used to determine whether the patient is breathing and, if so, whether the patient is currently inhaling or exhaling.

The camera 230 detects light and color information from the light. The camera 230 may be used to take photograph(s), which may be transmitted to a medical professional for analysis, or which may be automatically analyzed using software stored at the computer 200 or accessible via the network interface 210.

The thermometer 235 may be used to measure a body temperature of the patient. The body temperature may be used, alone or in conjunction with other data, to diagnose the patient, to determine a medical condition being experienced by the patient, or to provide a treatment recommendation for the patient.

The spirometer 240 includes a tool for measuring the volume of air inspired and expired by the lungs. The volume of air inspired and expired by the lungs may be used, alone or in conjunction with other data, to diagnose the patient, to determine a medical condition being experienced by the patient, or to provide a treatment recommendation for the patient.

The display device 245 may include a screen, a touchscreen, a projector, etc. The display device may be used to output visual information, such as text or images, to a user of the computer 200.

As shown, the components 210-245 of the computer 200 reside within the computer 200. However, one or more of the components 210-245 may reside externally to the computer 200 and may be connected to the computer 200 using a wired or wireless connection, such as a USB (universal serial bus) connection, a short-range radio connection (e.g., Bluetooth®), or a network connection. Furthermore, some examples of the subject technology may be implemented on a computer 200 that lacks access to one or more of the components 210-245, such as a computer lacking a thermometer 235 and a spirometer 240.

The memory 250 stores data and/or instructions. The memory 250 may include one or more of a short-term memory, a long-term memory, a cache unit, or a storage unit. As shown, the memory 250 includes sound measurements 255, thorax movement measurements 260, a medical condition determination module 265, and sound-movement-condition association data 270.

The sound measurements 255 include sound measurements measured by the microphone 220. Each sound measurement in the sound measurements 255 may be associated with a time measured by the clock 215. The thorax movement measurements 260 include inertial measurements associated with movement of a human thorax measured by the motion measurement unit 225. The thorax movement measurements 260 may include position measurements, speed measurements, velocity measurements, acceleration measurements, etc. Each thorax movement measurement in the thorax movement measurements 260 may be associated with a time measured by the clock 215. The thorax movement measurements 260 may correspond to inspiration or expiration of air from the lungs.

As both the sound measurements 255 and the thorax movement measurements 260 are associated with time(s), they may correlate with one another. For example, a thorax movement measurement may be associated with a sound measurement if both correspond to the same time or approximately the same time (e.g., within the same second, 0.5 seconds, 0.1 seconds, 0.05 seconds, etc.).

The sound-movement-condition correlation data 270 stores information associating medical condition diagnoses or medical treatment protocols with sound measurements and thorax movements. For example, a squawk at the end of inspiration in breathing is common to pneumonia, which may be treated by administering antibiotics. In another example, acoustic signals may be correlated with the breathing pattern to identify abnormal lung sounds, which may be associated with a lung disease. For example monitoring of asthma or COPD may help or be used in predicting of an exacerbation of the disease by changing patient's environment or drug regimen. As a result, the subject technology can be used to recommend a change in environment or a change in drug regimen for a patient suffering from asthma or COPD based on the thorax movement measurements 260 and the sound measurements 255.

The medical condition determination module 265 stores instructions which may be executed by the processing unit 205. When executing the medical condition determination module 265, the processing unit 205 receives the sound measurements 255 from the microphone 220. The processing unit 205 receives the thorax movement measurements 260 from the motion measurement unit 225 concurrently with receiving the sound measurements 255 from the microphone 220. The processing unit 205 determines a relationship between the sound measurements 255 and the thorax movement measurements 260, for example, based on the time(s), as measured by the clock 215, when the sound measurements 255 and the thorax movement measurements 260 were taken. The processing unit 205 determines a medical condition based on the relationship between the sound measurements 255 and the thorax movement measurements 260. The processing unit 205 provides an output representing the medical condition. The output may be provided using the display device 245. The medical condition may include, for example, a diagnosis, a treatment plan, a recommendation to administer a medication, or a recommendation to see a medical professional, such as a physician.

As discussed above, the medical condition is determined, at the medical condition determination module 265, based on the sound measurements 255 and the thorax movement measurements 260. In addition to the sound measurements 255 and the thorax movement measurements 260, other data may also be used to determine the medical condition. For example, the medical condition may be determined based on images of a human body captured by the camera 230, or a temperature measured by the thermometer 235 or a lung function measured by the spirometer 240.

As illustrated in FIG. 2, the medical condition determination module 265 and the sound-movement-condition association data 270 reside at the computer 200. However, in alternative implementations, the medical condition determination module 265 or the sound-movement-condition association data 270 may reside at a server distinct from the computer 200 and may be accessible to the computer 200 via a network through the network interface 210.

Figure 3:
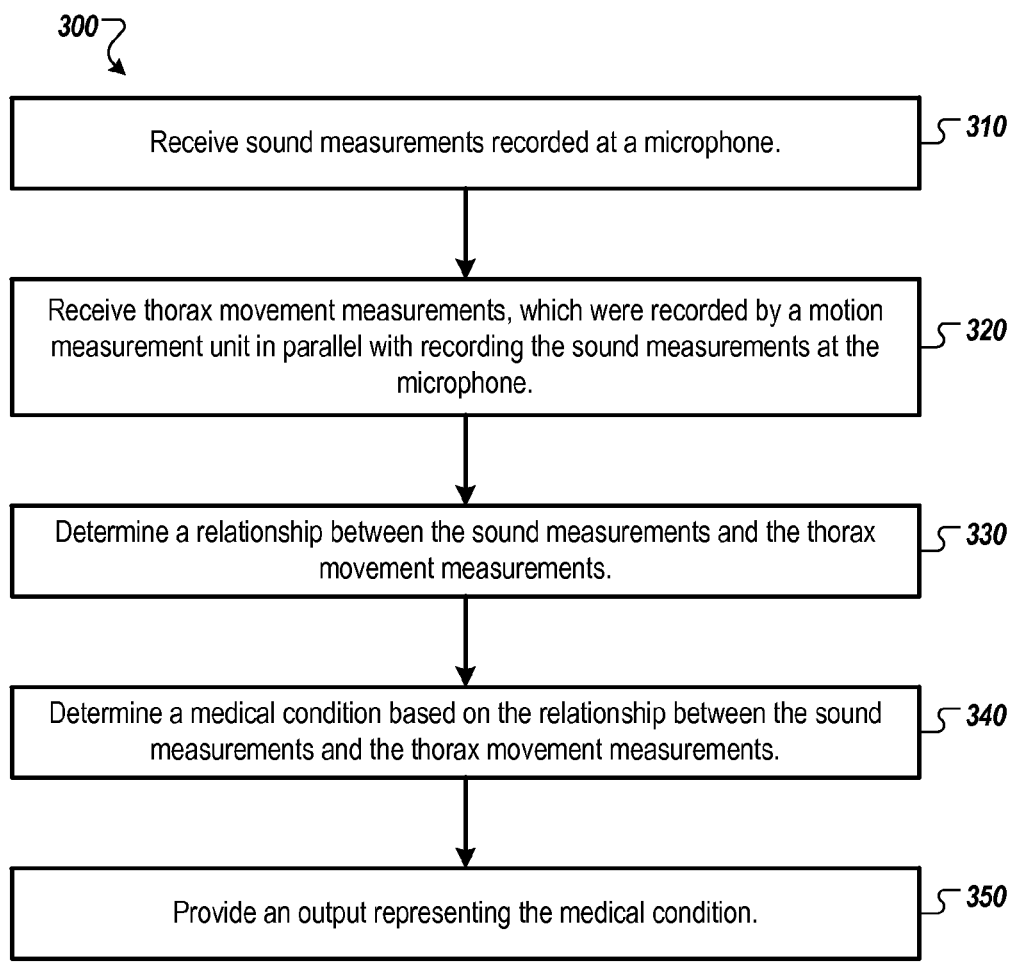
FIG. 3 illustrates, as a flow chart, an example process by which a medical condition may be determined based on sound measurements and thorax movement measurements.

FIG. 3 illustrates, as a flow chart, an example process 300 by which a medical condition may be determined based on sound measurements and thorax movement measurements.

The process 300 begins at step 310, where a computer (e.g., computer 200 or mobile computing device 130, or the "high-end" device described above) receives sound measurements recorded at a microphone. Each received sound measurement may be associated with a time measured by a clock.

In step 320, the computer receives thorax movement measurements, which were recorded by a motion measurement unit. The motion measurement unit may be an accelerometer, a speedometer, a velocity meter, etc. The thorax movement measurements may have been recorded in parallel with recording the sound measurements received in step 310. Each received thorax movement measurement may be associated with a time measured by a clock. The thorax movement measurements may include position measurements, speed measurements, velocity measurements, acceleration measurements, etc.

The sound measurements and the thorax movement measurements may be received from a single position on the patient's body, for example, the patient's left chest near the heart. Alternatively, the sound measurements and the thorax movement measurements may be taken from multiple different positions on the patient's body, for example, the left chest near the heart, the right chest, the left side of the back, the right side of the back, the left side below the armpit, the right side below the armpit, etc. In some cases, the computer may display, at the display device, instructions to place the computer or its housing a the multiple different positions on the patient's body. In some cases, the computer may request that a user input the age and the size (e.g., height, weight) of the patient. The multiple different positions may be determined based on the age and the size of the patient.

The device movement measurements may correspond to a human breathing pattern or a hand trembling pattern. The device movement measurements may correspond to the human breathing pattern if the position, velocity, or acceleration with respect to time have a regular, sinusoidal pattern. Otherwise, the thorax movement measurements may correspond to a hand trembling pattern.

If a hand trembling pattern is detected, the computer may display instructions to the user to reduce the hand trembling and to hold the computer or its housing more steadily. The computer may detect other evidence, based on the thorax movement measurements or the sound measurements, that the system is not being operated correctly. In these cases, the user may be informed, via the display device or via the speaker, of a correct mode of operation of the system. Alternatively, the user may receive, via the display device or via the speaker, a recommendation to consult a physician or a recommendation to receive training regarding the proper operation of the system.

The computer can verify, based on a combination of the thorax movement measurements and the sound measurements, that the patient is breathing deeper than normal. If the patient is not breathing deeper than normal, the computer may provide an output instructing the patient to adjust his breathing.

In step 330, the computer determines a relationship between the sound measurements and the thorax movement measurements. For example, the sound measurements and the thorax movement measurements may be correlated with one another based on the times when the sound measurements or the thorax movement measurements were taken. In an alternative implementation, the computer may transmit the sound measurements and the thorax movement measurements to a server, and the server may determine the relationship between the sound measurements and the thorax movement measurements.

The sound recorded by the microphone can correspond to lung sounds or to some extraneous noise or to voice or to rubbing artifacts or to intermittent contact artifacts. The computer can identify artifacts based on correlation between the sound and the thorax movement. For example, if acoustic signal is correlated with breathing pattern (e.g. crackles occur in-phase with breathing pattern), these crackles may be generated within lungs by pneumonia-related pathology. Alternatively, if acoustic signal is out-of-phase with breathing pattern (e.g. crackles occur in between the breathes), then these crackles may be an artifact of movement of chest piece against the skin. In this case, the computer may train the caregiver in the device application on the skin using either audio or visual output from a speaker or a display unit of the computer.

In step 340, the computer determines a medical condition based on the relationship between the sound measurements and the thorax movement measurements. The medical condition may include, for example, a diagnosis, a treatment plan, a recommendation to administer a medication, or a recommendation to see a medical professional, such as a physician. The medical condition may be determined, for example, based on the sound-movement-condition association data 270 of FIG. 2 or a similar data structure. In an alternative implementation, the server determines the medical condition and transmits the medical condition back to the computer.

In some cases, the computer may determine a sound type corresponding to the received sound measurements, and the medical condition may be determined based on the sound type and the relationship between the sound measurements and the thorax movement measurements. The sound type may include one or more of normal or abnormal bodily sounds, lung sounds, heart sounds, abdominal sounds, joint sounds or arterial flow sounds. The lung sounds include one or more of crackles, wheezes, rhonchi, squawks or vesicular sounds. The heart sounds include one or more of murmurs, clicks, S1, S2, S3 or S4. The abdominal sounds include borborygmi. The joint sounds include clicks and rubbing sounds. The arterial flow sounds include increased noise produced by turbulent flow of arterial blood passing through a region of stenosis.

The medical condition may include one or more of a diagnosis or a monitoring of pneumonia, asthma, congestive heart failure, chronic obstructive pulmonary disease (COPD), bronchitis, tuberculosis, acute respiratory distress syndrome, cystic fibrosis, bronchiolitis, asbestosis, cardiac abnormalities, intestinal obstruction, joint disorder, or arterial stenosis. The medical condition may include a drug recommendation and a titration (e.g., dosage) recommendation.

The medical condition may include a recommendation to contact a physician. In some cases, a network interface (e.g., network interface 210) of the computer may be used to transmit, with permission from the user, a representation of the received sound measurements or the received thorax movement measurements to the physician, so that the physician may analyze the sound measurements and the thorax movement measurements from his office. The transmission to the physician may include, for example, an email, mobile phone-based message, a voice telephone call, or a transmission via a medical organization's secure communication system.

In step 350, the computer provides an output representing the medical condition, which may have been generated either at the computer or at the server. The output may be provided as text or images via a display device or as audio via a speaker. In some cases, the computer may provide the output representing the medical condition to bot the user of the computer and to a remote physician, so that the physician may make additional diagnoses or treatment recommendations. After step 350, the process 300 ends.

Figure 4:
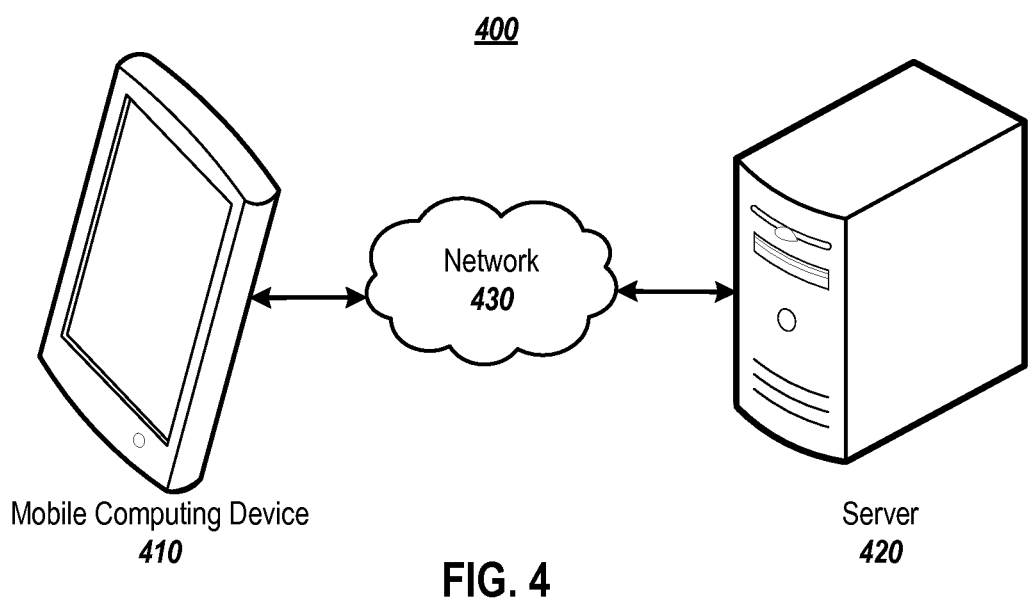
FIG. 4 illustrates an example client-server system for determining a medical condition based on sound measurements and thorax movement measurements.

FIG. 4 illustrates an example client-server system 400 for determining a medical condition based on sound measurements and thorax movement measurements. As shown, the client-server system 400 includes a mobile computing device 410 and a server 420 connected to one another via a network 430. The network 430 may include one or more of a local area network, a wide area network, a cellular network, a WiFi network, an Ethernet network, the Internet, an intranet, a virtual private network (VPN), etc. The mobile computing device 410 may correspond to the mobile computing device 130 or the computer 200 of FIGS. 1-2. The server 420 may include and implement the functionality of one or more of the medical condition determination module 265 or the sound-movement-condition association data 270 described in conjunction with FIG. 2, and may communicate with the mobile computing device 410 over the network 430.

Advantageously, as a result of the client-server system 400 illustrated in FIG. 4, one server 420 may store the medical condition determination module 265 and/or the sound-movement-condition association data 270 for multiple mobile computing devices 410 belonging to many different people. As a result, memory and processing capability requirements at the mobile computing device(s) may be minimized.

In addition, upon determining a medical condition, the server 420 may transmit the medical condition information to both the mobile computing device 410 and to a physician for further diagnosis or treatment recommendations. In some cases, the server 420 may provide the medical condition information to a physician for review before transmitting it back to the mobile computing device 410.

Figure 5:
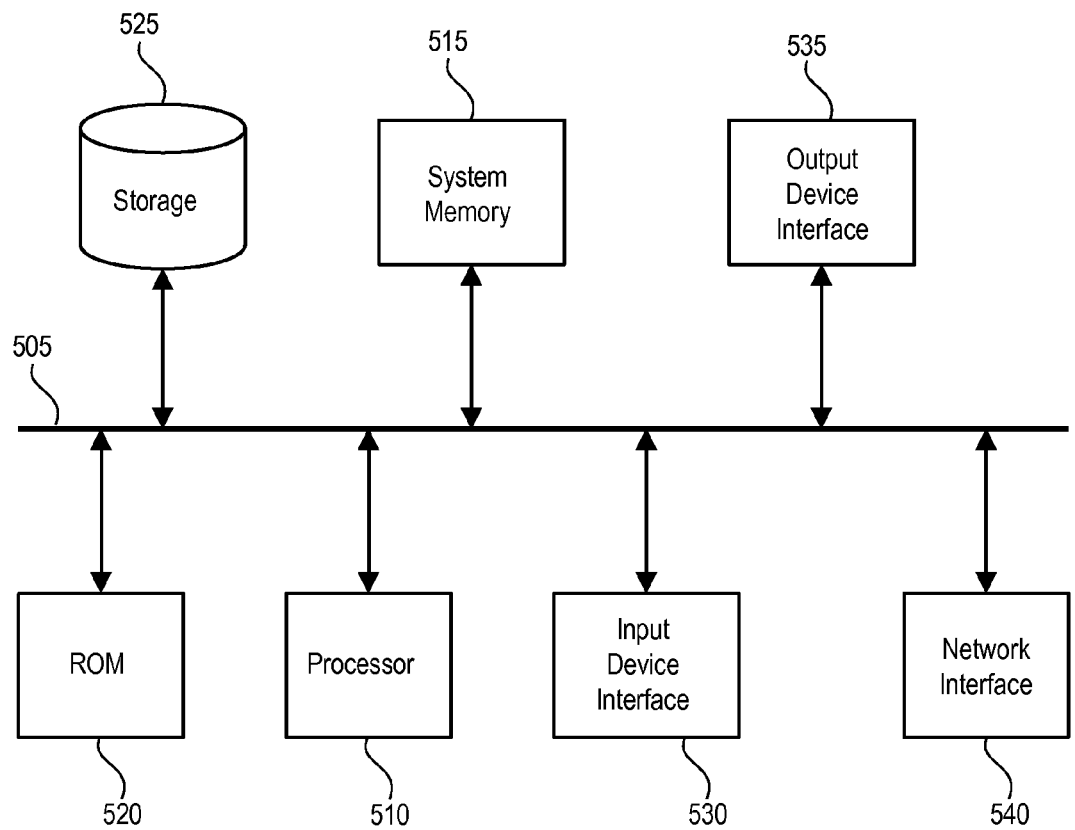
FIG. 5 conceptually illustrates an example electronic system with which some implementations of the subject technology are implemented.

FIG. 5 conceptually illustrates an electronic system 500 with which some implementations of the subject technology are implemented. For example, one or more of the mobile computing device 130, the computer 200, the mobile computing device 410 or the server 420 may be implemented using the arrangement of the electronic system 500. The electronic system 500 can be a computer (e.g., a mobile phone, PDA), or any other sort of electronic device. Such an electronic system includes various types of computer readable media and interfaces for various other types of computer readable media. Electronic system 500 includes a bus 505, processor(s) 510, a system memory 515, a read-only memory 520, a permanent storage device 525, an input device interface 530, an output device interface 535, and a network interface 540.

The bus 505 collectively represents all system, peripheral, and chipset buses that communicatively connect the numerous internal devices of the electronic system 500. For instance, the bus 505 communicatively connects the processor(s) 510 with the read-only memory 520, the system memory 515, and the permanent storage device 525.

From these various memory units, the processor(s) 510 retrieves instructions to execute and data to process in order to execute the processes of the subject technology. The processor(s) can include a single processor or a multi-core processor in different implementations.

The read-only-memory (ROM) 520 stores static data and instructions that are needed by the processor(s) 510 and other modules of the electronic system. The permanent storage device 525, on the other hand, is a read-and-write memory device. This device is a non-volatile memory unit that stores instructions and data even when the electronic system 500 is off. Some implementations of the subject technology use a mass-storage device (for example a magnetic or optical disk and its corresponding disk drive) as the permanent storage device 525.

Other implementations use a removable storage device (for example a floppy disk, flash drive, and its corresponding disk drive) as the permanent storage device 525. Like the permanent storage device 525, the system memory 515 is a read-and-write memory device. However, unlike storage device 525, the system memory 515 is a volatile read-and-write memory, such a random access memory. The system memory 515 stores some of the instructions and data that the processor needs at runtime. In some implementations, the processes of the subject technology are stored in the system memory 515, the permanent storage device 525, or the read-only memory 520. For example, the various memory units include instructions for detecting a medical condition in accordance with some implementations. From these various memory units, the processor(s) 510 retrieves instructions to execute and data to process in order to execute the processes of some implementations.

The bus 505 also connects to the input and output device interfaces 530 and 535. The input device interface 530 enables the user to communicate information and select commands to the electronic system. Input devices used with input device interface 530 include, for example, alphanumeric keyboards and pointing devices (also called "cursor control devices"). Output device interfaces 535 enables, for example, the display of images generated by the electronic system 500. Output devices used with output device interface 535 include, for example, printers and display devices, for example cathode ray tubes (CRT) or liquid crystal displays (LCD). Some implementations include devices for example a touch screen that functions as both input and output devices.

Finally, as shown in FIG. 5, bus 505 also couples electronic system 500 to a network (not shown) through a network interface 540. In this manner, the electronic system 500 can be a part of a network of computers (for example a local area network (LAN), a wide area network (WAN), or an Intranet, or a network of networks, for example the Internet. Any or all components of electronic system 500 can be used in conjunction with the subject technology.

The above-described features and applications can be implemented as software processes that are specified as a set of instructions recorded on a computer readable storage medium (also referred to as computer readable medium). When these instructions are executed by one or more processor(s) (which may include, for example, one or more processors, cores of processors, or other processing units), they cause the processor(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage or flash storage, for example, a solid-state drive, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra density optical discs, any other optical or magnetic media, and floppy disks. The computer-readable media can store a computer program that is executable by at least one processor and includes sets of instructions for performing various operations. Examples of computer programs or computer code include machine code, for example is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some aspects of the disclosed subject matter, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, an "aspect" does not imply that the aspect is essential to the subject technology or that the aspect applies to all configurations of the subject technology. A disclosure relating to an aspect may apply to all configurations, or one or more configurations. A phrase, for example, an aspect may refer to one or more aspects and vice versa. A phrase, for example, a "configuration" does not imply that such configuration is essential to the subject technology or that such configuration applies to all configurations of the subject technology. A disclosure relating to a configuration may apply to all configurations, or one or more configurations. A phrase, for example, a configuration may refer to one or more configurations and vice versa.

What is claimed is:

1. A system comprising:
one or more processors; and
a memory comprising instructions which, when executed by the one or more processors, cause the one or more processors to:
present, via a display unit, instructions to place a device housing a microphone and a motion measurement unit at a plurality of positions on a human body of a subject, the plurality of positions being determined based on an age and a size of the subject, the instructions being displayed on a part of the display unit not covered by a sleeve of a hand of a user;
receive sound measurements recorded at the microphone;
receive thorax movement measurements recorded by the motion measurement unit concurrently with recording the sound measurements at the microphone, the sound measurements and the thorax movement measurements being taken at the plurality of positions on the human body;
determine a sound type corresponding to the received sound measurements;
determine a relationship between the sound measurements and the thorax movement measurements;
determine a medical condition based on the sound type and the relationship between the sound measurements and the thorax movement measurements; and
provide an output representing the medical condition.

2. The system of claim 1, wherein:
the sound type comprises one or more of normal or abnormal bodily sounds, lung sounds, heart sounds, abdominal sounds, joint sounds or arterial flow sounds;
the lung sounds comprise one or more of crackles, wheezes, rhonchi, squawks or vesicular sounds, wherein the heart sounds comprise one or more of murmurs, clicks, S1, S2, S3 or S4;

the abdominal sounds comprise borborygmi;

the joint sounds comprise clicks and rubbing sounds; and the arterial flow sounds comprise increased noise produced by turbulent flow of arterial blood passing through a region of stenosis.

3. The system of claim 1, wherein the thorax movement measurements correspond to a human breathing pattern or a hand trembling pattern.

4. The system of claim 1, further comprising the display unit.

5. The system of claim 1, wherein the plurality of positions on the human body comprise a chest position, a back position, and a side position.

6. The system of claim 1, wherein the medical condition comprises a diagnosis or a monitoring of pneumonia, asthma, congestive heart failure, chronic obstructive pulmonary disease (COPD), bronchitis, tuberculosis, acute respiratory distress syndrome, cystic fibrosis, bronchiolitis, asbestosis, cardiac abnormalities, intestinal obstruction, joint disorder, or arterial stenosis.

7. The system of claim 1, wherein the medical condition comprises a drug recommendation and a titration recommendation.

8. The system of claim 1, wherein the medical condition comprises a recommendation to contact a physician.

9. The system of claim 8, further comprising a network interface, the memory further comprising instruction which, when executed by the one or more processors, cause the one or more processors to:

transmit, using the network interface, a representation of the received sound measurements or the received thorax movement measurements to the physician.

10. The system of claim 1, the memory further comprising instruction which, when executed by the one or more processors, cause the one or more processors to:

verify, based on a combination of the thorax movement measurements and the sound measurements, that a patient is breathing deeper than normal or not breathing.

11. The system of claim 1, the memory further comprising instruction which, when executed by the one or more processors, cause the one or more processors to:

verify, based on the thorax movement measurements and the sound measurements, whether the system is being operated correctly; and in a case where the system is not being operated correctly, inform a user of a correct mode of operation of the system or recommend consulting a physician.

12. The system of claim 1, wherein the medical condition is determined based on images of a human body captured by a camera, or a temperature measured by a thermometer or a lung function measured by a spirometer.

13. A non-transitory computer-readable medium comprising instructions which, when executed by a computer, cause the computer to:

present, via a display unit, instructions to place a device housing a microphone and a motion measurement unit at a plurality of positions on a human body of a subject, the plurality of positions being determined based on an age and a size of the subject, the instructions being displayed on a part of the display unit not covered by a sleeve of a hand of a user;

receive sound measurements recorded at the microphone;

receive thorax movement measurements recorded by the motion measurement unit in parallel with recording the sound measurements at the microphone, the sound measurements and the thorax movement measurements being taken at the plurality of positions on the human body;

determine a sound type corresponding to the received sound measurements;

determine a relationship between the sound measurements and the thorax movement measurements;

determine a medical condition based on the sound type and the relationship between the sound measurements and the thorax movement measurements; and provide an output representing the medical condition.

14. The non-transitory computer-readable medium of claim 13, wherein:

the sound type comprises one or more of normal or abnormal bodily sounds, lung sounds, heart sounds, abdominal sounds, joint sounds or arterial flow sounds;

the lung sounds comprise one or more of crackles, wheezes, rhonchi, squawks or vesicular sounds, wherein the heart sounds comprise one or more of murmurs, clicks, S1, S2, S3 or S4;

the abdominal sounds comprise borborygmi;

the joint sounds comprise clicks and rubbing sounds; and the arterial flow sounds comprise increased noise produced by turbulent flow of arterial blood passing through a region of stenosis.

15. A computer-implemented method comprising:

presenting, via a display unit, instructions to place a device housing a microphone and a motion measurement unit at a plurality of positions on a human body of a subject, the plurality of positions being determined based on an age and a size of the subject, the instructions being displayed on a part of the display unit not covered by a sleeve of a hand of a user;

receiving, at one or more processors, sound measurements generated at the microphone;

receiving thorax movement measurements recorded by the motion measurement unit in parallel with recording the sound measurements at the microphone, the sound measurements and the thorax movement measurements being taken at the plurality of positions on the human body;

determining a sound type corresponding to the received sound measurements;

determining a relationship between the sound measurements and the thorax movement measurements;

determining a medical condition based on the sound type and the relationship between the sound measurements and the thorax movement measurements; and providing an output representing the medical condition.

\* \* \* \* \*